United States Patent
Yanagita et al.

(10) Patent No.: US 7,393,668 B2
(45) Date of Patent: *Jul. 1, 2008

(54) METHOD OF COLLECTING HIGHLY PURE POLYHYDROXYALKANOATE FROM MICROBIAL CELLS

(75) Inventors: Yoshifumi Yanagita, Akashi (JP); Noriko Ogawa, Kobe (JP); Yasuyoshi Ueda, Himeji (JP); Fumio Osakada, Okayama (JP); Keiji Matsumoto, Nishinomiya (JP)

(73) Assignee: Kaneka Corporation, Osaka-shi (JP)

( * ) Notice: Subject to any disclaimer, the term of this patent is extended or adjusted under 35 U.S.C. 154(b) by 298 days.

This patent is subject to a terminal disclaimer.

(21) Appl. No.: 10/541,389

(22) PCT Filed: Jan. 20, 2004

(86) PCT No.: PCT/JP2004/000416

§ 371 (c)(1),
(2), (4) Date: Jul. 1, 2005

(87) PCT Pub. No.: WO2004/065608

PCT Pub. Date: Aug. 5, 2004

(65) Prior Publication Data

US 2006/0084161 A1    Apr. 20, 2006

(30) Foreign Application Priority Data

Jan. 20, 2003    (JP) .............................. 2003-011099

(51) Int. Cl.
*C12P 7/62* (2006.01)
*C12N 9/00* (2006.01)

(52) U.S. Cl. ........................................ 435/135; 435/183

(58) Field of Classification Search ................. 435/135, 435/183; 528/361, 493, 496
See application file for complete search history.

(56) References Cited

U.S. PATENT DOCUMENTS

| | | | | |
|---|---|---|---|---|
| 4,358,583 A | * | 11/1982 | Walker et al. | 528/491 |
| 4,477,654 A | * | 10/1984 | Holmes et al. | 528/361 |
| 5,213,976 A | * | 5/1993 | Blauhut et al. | 435/135 |
| 6,808,907 B2 | * | 10/2004 | Honma et al. | 435/135 |

FOREIGN PATENT DOCUMENTS

| | | |
|---|---|---|
| EP | 0046017 * | 2/1982 |
| JP | 55-118394 | 9/1980 |
| JP | 57-65193 | 4/1982 |
| JP | 63-198991 | 8/1988 |
| JP | 2-69187 | 3/1990 |
| JP | 5-507410 | 10/1993 |
| JP | 5-336982 | 12/1993 |
| JP | 7-31487 | 2/1995 |
| JP | 07-031487 | 2/1995 |
| JP | 7-31488 | 2/1995 |
| JP | 7-31489 | 2/1995 |
| JP | 07-031489 | 2/1995 |
| JP | 7-79788 | 3/1995 |
| JP | 4-61638 | 7/1995 |
| JP | 7-509131 | 10/1995 |
| JP | 8-502415 | 3/1996 |
| JP | 11-266891 | 10/1999 |
| JP | 2001-046094 | 2/2001 |
| JP | 20001-46094 | 2/2001 |
| JP | 2001-57895 | 3/2001 |
| JP | 2001-057895 | 3/2001 |
| WO | WO 92/22659 | 12/1992 |

OTHER PUBLICATIONS

Harrison et al "Combined chemical and mechanical processes for the disruption of bacteria" Bioseparaton 2: pp. 95-105.*
Jong-il Choi et al.: Efficient and Economic Recovery of poly(3-Hydroxybutyrate) from recombinant *Escherichia coli* by simple digestion with chemicals, Biotechnol. Bioeng. (1999), vol. 62, No. 5, pp. 546 to 553.

* cited by examiner

*Primary Examiner*—Herbert J Lilling
(74) *Attorney, Agent, or Firm*—Kenyon & Kenyon LLP

(57) ABSTRACT

The present invention has an object to provide a method for separating and purifying a PHA without causing a serious decrease of the molecular weight to obtain a highly pure PHA in a high yield, which comprises efficiently removing cell components other than PHA particles from a cultured PHA-containing microbial cell. Another object of the present invention is to provide a method for obtaining an agglomerate of PHA particles.

The method for recovering a PHA according to the present invention is a method which comprises efficiently disrupting a cell to recover the PHA by carrying out a physical disruption treatment and an alkali addition at low temperature for an aqueous suspension of the PHA-containing microbial cell, and then treating the PHA with an enzyme and/or a surfactant. Moreover, the particle diameter of the PHA may be enlarged by suspending the PHA in a hydrophilic solvent and/or water, and stirring at a temperature equal to or below the boiling point of said suspension, to agglomerate said PHA.

20 Claims, 1 Drawing Sheet

METHOD OF COLLECTING HIGHLY PURE POLYHYDROXYALKANOATE FROM MICROBIAL CELLS

This is a 371 national phase application of PCT/JP2004/000416 filed 20 Jan. 2004, claiming priority to Japanese Application No. 2003-011099 filed 20 Jan. 2003, the contents of which are incorporated herein by reference.

TECHNICAL FIELD

The present invention relates to a separation/recovery method of a biodegradable polyester resin from microbial cells, and to an agglomeration method of said resin particle.

BACKGROUND ART

Polyhydroxyalkanoates (hereinafter referred to briefly as "PHA"s) are thermoplastic polyesters which are synthesized and stored as an energy storage substance in cells of a variety of microorganisms. The PHAs, which are produced by microorganisms using natural organic acids or oils as carbon sources, are completely biodegraded by a microorganism in soil or water to be taken up in the carbon cycle of the natural world. Therefore, PHAs can be said to be an environment-conscious plastic material which hardly causes adverse effects for ecological system. In these years, a synthetic plastic came into a serious social problem in view of environment pollution, waste disposal and oil resource, thus the PHA has attracted attention as an eco-friendly green plastic and its practical applications are longed for. Also in the field of medical treatment, it is considered possible to use PHAs as implant materials which do not require recovery, or vehicles for drug. Thus, practical applications thereof have been expected.

Since PHAs synthesized by a microorganism are stored in cells usually in the form of granules, it is required a procedure for separating PHAs from microbial cells to utilize them as plastics. The known technology for separation and purification of PHAs from microbial cells can be roughly classified into technologies which comprise extracting a PHA from microbial cells with organic solvents capable of solving a PHA and technologies which comprise removing cell components other than PHAs by cell disruption or solubilization.

In earlier researches, many technologies for separating and purifying PHAs by extraction using organic solvents were reported (see Japanese Kokai Publication Sho-55-118394, Japanese Kokai Publication Sho-57-65193, Japanese Kokai Publication Sho-63-198991, Japanese Kokai Publication Hei-02-69187 and Japanese Kokai Publication Hei-07-79788). In these reports, halogen compounds such as chloroform were used as organic solvents having the highest solubility of PHAs, but when a PHA was dissolved in such a solvent, viscosity of solution became very high and handling of the solution became difficult. Therefore, for extracting a PHA, it was needed to set the polymer concentration in a range as extremely low as about 2 to 3%, thus significantly large amount of solvent was required. In addition, for crystallizing a PHA from a solvent layer in a high yield, a large amount as 4 to 5 times as the above solvent of poor solvents for a PHA, such as methanol and hexane, were separately required. Accordingly, for production on an industrial scale, large-scale equipment is required. Moreover, a PHA cannot be produced in a low cost since these technologies require huge amount of solvent, and therefore it takes much cost for solvent recovery and cost due to solvent loss. Due to such reasons as mentioned above, these methods have not been put into practice.

On the other hand, various technologies have been reported which comprise solubilizing and removing cell components other than PHAs by chemical treatments or physical disruption treatments to recover PHAs in the form of granules.

As a method for chemically treating a microbial cell (hereinafter, sometimes referred to as "cell"), J. Gen. Microbiology, 1958 vol. 19, p. 198-209 discloses a technology which comprises treating a suspension of a microbial cell with sodium hypochlorite and solubilizing cell components other than a PHA to recover the PHA. In this technology, marked degradation of a PHA is caused in solubilizing the cell components other than the PHA, and processing ways into products are limited. Moreover, sensible smell of chlorine is left behind in PHAs, which is undesirable for a polymer product. Thus, this technology is not considered to be suitable for practical use. Japanese Kokoku Publication Hei-04-61638 discloses a recovering process which comprises heat treatment in combination with use of an enzyme and/or a surfactant. In this process, heating a suspension to 100° C. or above beforehand is required to decompose nucleic acids, since the suspension becomes highly viscous by free nucleic acids when cells are dissolved by an enzyme treatment. However, the molecular weight of a PHA decreases markedly by heating to 100° C. or above, and an application to products will become impossible. Moreover, despite this technology is very complicated and requires many processes, purity of an obtained PHA is as much as about 88% in general, and 97% even at the maximum. Additionally, a technology which comprises treating a PHA-containing microbial cell with a surfactant, decomposing a nucleic acid released from the cell with hydrogen peroxide at 80° C. for 3 hours, and separating a PHA with a purity of 99% (see Japanese Kohyo Publication Hei-08-502415), and a technology which comprises heating a suspension of a PHA-containing microorganism to 50° C. or higher under a strongly acidic condition of below pH 2, and separating a PHA (see Japanese Kokai Publication Hei-11-266891) have been proposed. Under these heating conditions, the molecular weight of the PHA decreases remarkably, therefore even if its purity is improved, applications to products are still impossible.

On the other hand, as a method applying physical disruption treatments, a technology have been reported, which comprises carrying out an alkali addition with a high-pressure disruption or a combination of a high-pressure disruption. Although "Bioseparation", 1991, vol. 2, p. 95-105 does not describe purity or yield of a polymer, cell components remain in a poly-3-hydroxybutyrate (PHB) fraction and the purity of PHB is presumably not high since high-pressure disruption is carried out under a condition where pH is returned to neutral after adding alkali to a cell suspension containing PHB. Japanese Kokai Publication Hei-07-31487 discloses a technology which comprises heating to 80° C. after an alkali addition to a cell suspension containing a PHA, stirring the mixture for 1 hour and recovering a polymer by centrifugation; Japanese Kokai Publication Hei-07-31488a discloses a technology which comprises carrying out high-pressure disruption at 70° C.; and a technology considered to develop the method described in the above "Bioseparation", 1991, vol. 2, p. 95-105, that is a technology which comprises carrying out high-pressure disruption at 70° C. or higher after the alkali addition in Japanese Kokai Publication Hei-07-31489, respectively. By these technologies, since the processes are carried out in high temperature conditions, there is a tendency toward remarkable decrease in a molecular weight of a PHA in some conditions. Moreover, purity is also as low as about 66 to 85%, thus these technologies may not be applied to actual industrial processes.

As mentioned above, we can find it very difficult to recover a PHA from a cultured cell without decreasing the molecular weight but with high purity and a high yield in a low-cost on an industrial production.

By the way, when a PHA is obtained by a technology comprising solubilizing to remove cell components other than a PHA by a chemical or physical treatment and recovering the PHA in the form of granules, the obtained PHA usually occurred as a form of fine particles having diameters of several microns. It is more difficult to separate such fine particles from a liquid medium as compared with the case of particles having a larger diameter. Moreover, these fine particles are considered to have problems such as a risk to cause dust explosion and/or accumulation in lungs when aspirated, thus care should be taken for handling.

In order to avoid these problems, there have been attempts to enlarge the particle diameter by agglomerating a PHA. For example, an agglomeration method by heating or an alkaline metal salt has been developed. As a method of agglomeration by heating, a technology is disclosed, which comprises agglomerating PHB by heating a PHB-containing suspension to the vicinity of the melting point of PHB (180° C.) (see Bailey, Neil A.; George, Neil; Niranjan, K.; Varley, Julie. Biochemical Engineering group, University Reading, "I Chem E Res. Event, Eur. Conf. Young Res. Chem. Eng." (Britain), 2nd edition, Institution of Chemical Engineers, 1996, vol. 1, p. 196-198). Moreover, Japanese Kohyo Publication Hei-07-509131 discloses a technology to enlarge a particle diameter of a copolymer comprised of 3-hydroxybutyrate (3HB) and 3-hydroxyvalerate (3HV) (hereinafter such copolymer is referred to as "PHBV"), which comprises injecting steam with an appropriate temperature and pressure directly into an aqueous suspension of PHBV, and heating -and stirring the suspension at 120 to 160° C. However, they are not practical since these technologies require heating at a high temperature, the molecular weight of PHA decreases remarkably, and further special equipment with a pressure resistance is required. Alternatively, as a method for agglomerating a PHA by adding an alkaline metal salt, a technology for agglomeration using a divalent cation (see J. Biotechnol., 1998, vol. 65 (2, 3), p. 173-182, and Japanese Kohyo Publication Hei-05-0507410) has been disclosed. However, these technologies are not preferable in, for example, that polymer agglomeration strength is not always high, that a metal salt is contaminated into a polymer, and the like ploblems. Alternatively, a technology which comprises agglomerating PHB by blowing ultrafine bubbles into a PHB suspension to raise a flock to the surface (see Spec. Publ.-R. Soc. Chem., 1994, vol. 158 (Separations for Biotechnology 3), p. 113-119) has also been reported. However, the agglomerate obtained by this technology has a diameter of 2 to 45 μm, and cannot be said as a sufficient size.

Thus, any methods for controlling a molecular-weight decrease of a PHA and carrying out agglomeration effectively have not been known in the state of the art.

As described above, there lies a large obstacle for practical applications in studies of PHAs, which are one species of biodegradable polymers derived from microorganisms, since any processes with low costs and suitable for industrial productions have not been established respectively in recovering PHAs from microbial cells, and further in agglomerating PHA particles carried out according to need.

SUMMARY OF THE INVENTION

As mentioned above, in the process of recovering a PHA from a microbial cell, conventional methods cannot be said as processes with low costs and suitable for industrial productions. Moreover, the present inventors have carried out a preliminary investigation, and as a result, they found that such conventional methods, which require a chemical treatment by hypochlorous acid, hydrogen peroxide, acid, a large amount of alkali, etc., and a reaction under a high temperature, could hardly be utilized. Especially in the case that a PHA composed two or more species of monomer components was used, the molecular weight tends to decrease more remarkably than the case of using a homopolymer PHB.

Therefore, the object of the present invention is to solve the above-mentioned problems in the conventional methods, and to provide a method for separating and purifying a PHA through fewer steps without causing a serious decrease of the molecular weight to obtain a highly pure PHA in a high yield, which comprises efficiently removing cell components other than PHA particles from a cultured PHA-containing microbial cell. Another object of the present invention is to provide a method for obtaining an agglomerate of PHA particles.

The present inventors carried out intensive investigations on an industrially advantageous recovery method of a PHA from a microbial cell. As a result thereof, the inventors found it possible to efficiently recover highly pure PHA by producing a PHA using a microorganism, adding an alkali to an aqueous suspension of the microbial cell containing a PHA while stirring and carrying out physical disruption treatment at comparatively low temperature, then recovering the PHA, treating the PHA with an enzyme and/or surfactant in an aqueous suspension or wet state, and further washing said PHA with a hydrophilic solvent and/or water. Furthermore, the inventors also found it possible to enlarge a particle diameter of a PHA by suspending the PHA in a hydrophilic solvent and/or water and agglomerating them by stirring at a temperature equal to or below the boiling point of said suspension. By these methods, the inventors have succeeded in preventing the molecular weight decrease, which has been a very difficult subject up to present, and in recovering a PHA having purity of 99% or more in a yield of 90% or more. By further agglomeration, the inventors have completed the production method of a PHA capable of avoiding difficulty of handling and/or the risk of dust explosion. By the completion of the present invention, practical applications of a biodegradable polymer derived from a microbial cell will become possible.

That is, the present invention relates to a method for recovering a PHA from a PHA-containing microbial cell which comprises;

(a) a step comprising adding an alkali to an aqueous suspension of the PHA-containing microbial cell while stirring and carrying out a physical disruption treatment to disrupt the cell, solubilizing or emulsifying cell substances other than the PHA in said cell, and then separating the PHA from the aqueous suspension, and (b) a step comprising treating the separated PHA with an enzyme and/or a surfactant to solubilize impurities adhering to the PHA or to solubilize them after decomposing, and then washing the PHA with a hydrophilic solvent and/or water.

Moreover, the present invention relates to the above-mentioned method for recovering a PHA which further comprises;

(c) a step comprising suspending the washed PHA in a hydrophilic solvent and/or water and stirring at a temperature equal to or below the boiling point of said suspension and agglomerating the PHA to enlarge the particle diameter thereof, and then separating the agglomerated PHA from the suspension.

EXPLANATION OF NUMERALS

Figure 1:
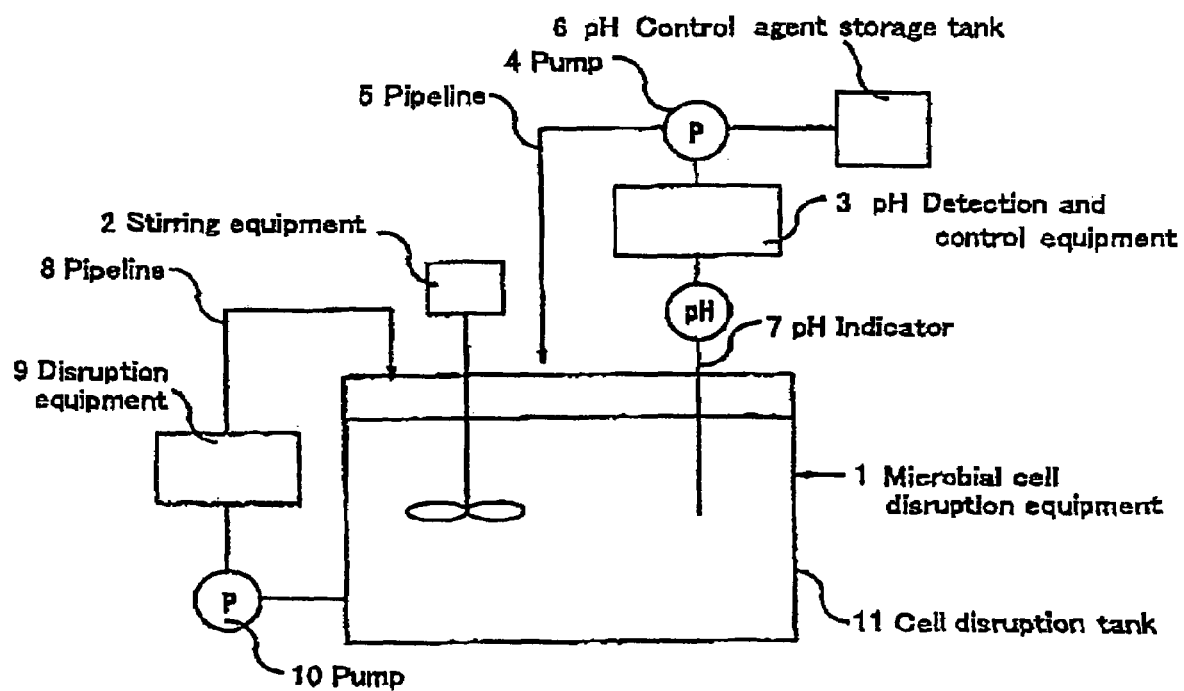
FIG. 1 represents an explanatory drawing showing a microbial cell disruption equipment used for separating and purifying a poly-3-hydroxyalkanoic acid according to the present invention.

1 Microbial cell disruption equipment
2 Stirring equipment
3 pH Detection and control equipment
4 Pump
5 Pipeline
6 pH Control agent storage tank
7 pH Indicator
8 Pipeline
9 Disruption equipment
10 Pump
11 Cell disruption tank

DETAILED DESCRIPTION OF THE INVENTION

Hereinafter, the present invention will be described in further detail with a preferable embodiment.

The method for recovering polyhydroxyalkanoate according to the present invention comprises the following steps (a) and (b);

(a) a step comprising adding an alkali to an aqueous suspension of a polyhydroxyalkanoate-containing microbial cell while stirring and carrying out a physical disruption treatment to disrupt the cell, and solubilizing or emulsifying cell substances other than the polyhydroxyalkanoate in said cell, and then separating the polyhydroxyalkanoate from the aqueous suspension, and (b) a step comprising treating the separated polyhydroxyalkanoate with an enzyme and/or a surfactant to solubilize impurities adhering to the polyhydroxyalkanoate or to solubilize them after decomposing, and then washing the polyhydroxyalkanoate with a hydrophilic solvent and/or water.

Firstly, a polyhydroxyalkanoate (PHA) as used in this specification is a generic term meaning any or all polymers composed of hydroxyalkanoates. The hydroxyalkanoate components are not particularly restricted, but specifically there may be mentioned, for example, 3-hydroxybutyrate (3HB), 3-hydroxyvalerate (3HV), 3-hydroxypropionate, 4-hydroxybutyrate, 4-hydroxyvalerate, 5-hydroxyvalerate, 3-hydroxypentanoate, 3-hydroxyhexanoate (3HH), 3-hydroxyheptanoate, 3-hydroxyoctanoate, 3-hydroxynonanoate, 3-hydroxydecanoate, etc.

The PHA of the present invention may be a homopolymer of one of these hydroxyalkanoates or a copolymer obtainable by copolymerizing two or more species of these. Particularly, the recovering method of the present invention is suitable since the molecular weight hardly decreases, as described below, in the case of using a copolymer, whose molecular weight tends to be decreased in a conventional method.

As specific examples of the PHA, there may be mentioned PHB (a homopolymer of 3HB), PHBV (a binary copolymer composed of 3HB and 3HV), PHBH (a binary copolymer composed of 3HB and 3HH, see Japanese Patent Publication No. 2777757), PHBHV (aternary copolymer composed of 3HB, 3HV and 3HH, see Japanese Patent Publication No. 2777757), etc. Particularly among them, a copolymer comprising 3HH as a monomer unit is preferable since it has degradability as a biodegradable polymer and softness, and more preferably PHBH.

In the case of PHBH, The compositional ratio of monomer units constituting PHBH is not particularly restricted but ones containing 1 to 99mol % of 3HH unit are preferred and ones containing 3 to 30% of 3HH are more preferred since they show preferable workability. Moreover, in the case of PHBHV, the compositional ratio of monomer units constituting of PHBHV is not particularly restricted, but ones containing 1 to 95 mol % of 3HB unit, 1 to 96 mol % of 3HV unit, and 1 to 30 mol % of 3HH unit are preferred.

From a practical point of view, it is preferred that the PHA has the average molecular weight determined by a gel chromatography method, in which polystyrene is set as a molecular weight standard, of 10,000 or more. It is more preferred 50,000 or more, still more preferably 100,000 or more, and particularly preferably 200,000 or more.

The microorganism to be used in the present invention is not particularly restricted provided that it is a microorganism capable of storing a PHA in cells. For example, there may be mentioned microorganisms belonging to the genus *Aeromonas, Alcaligenes, Azotobacter, Bacillus, Clostridium, Halobacterium, Nocardia, Rhodospirillum, Pseudomonas, Ralstonia, Zoogloea*, etc. More specifically, there may be mentioned *Aeromonas caviae*, etc. as a microorganism belonging to the genus *Aeromonas, Alcaligenes lipolytica, Alcaligenes latus*, etc. as ones belonging to the genus *Alcaligenes*, and *Ralstonia eutropha*, etc. as a microorganism belonging to the genus *Ralstonia*, for instance.

These microorganisms can store a PHA in cells by controlling culture conditions.

Alternatively, a transformant transformed with a gene group involving a PHA synthesis may also be used as these microorganisms. In that case, the host is not particularly restricted, and there may be mentioned microorganisms such as *Escherichia coli* (the genus *Escherichia*) and yeast belonging to the genus *Candida, Saccharomyces, Yarrowia*, etc. (WO 0188144), in addition to the above-mentioned microorganisms.

Among the above microorganisms to be used in the present invention, *Aeromonas caviae* belonging to the genus *Aeromonas* and the transformant transformed with a PHA synthase group gene derived from said *Aeromonas caviae* are preferable since they have an excellent synthesizing ability of PHBH. In particular, more preferred is a transformant obtained by introducing a PHA synthase group gene derived from *Aeromonas caviae* into *Ralstonia eutropha*.

As one example of said microorganisms, *Ralstonia eutropha* PHB-4/pJRDEE32d13 strain obtained by introducing a PHA synthase group gene derived from *Aeromonas caviae* into *Ralstonia eutropha* may preferably be used. Said *Ralstonia eutropha* PHB-4/pJRDEE32d13 strain is internationally deposited based on Budapest Treaty to National Institute of Advanced Industrial Science and Technology International Patent Organism Depositary, Tsukuba, Central 6, 1-1-1 Higashi, Ibaraki, Japan on Aug. 7, 1997 (Heisei-9), with an accession No. FERM BP-6038 under the name of *Alcaligenes eutrophus* AC32.

In the practice of the present invention, microbial cells obtained by culturing microorganisms mentioned above in a suitable condition to store a PHA therein, is utilized. The above culturing method is not particularly restricted but the method known to the person skilled in the art, for example the method described in Japanese Kokai Publication 2001-340078, can be applied.

In recovering a PHA, it is naturally preferable that the PHA content in the cultured microbial cell is higher. In the application for an industrial production, PHA content in dried cells is preferably 50 weight % or more. Taking subsequent separation operations and purity of a separated polymer into consideration, the PHA content in dried cells is more preferably 60 weight % or more, and still more preferably 70 weight % or more.

Although it is possible to directly proceed to the step (a) after completion of the culture, it is also possible to proceed to the step (a) after recovering cells by methods such as centrifugation and membrane separation, which are known to the person skilled in the art, or recovering cells after killing cells by heating and the like procedure. The temperature for the heating is preferably 50° C. to 70° C.

In the step (a) of the present invention, it is important to add an alkali to an aqueous suspension of a PHA-containing microbial cell while stirring and carrying out physical disruption treatment of the aqueous suspension. That is, a process is actually carried out, which comprises (1) preparing an aqueous suspension of the PHA-containing microbial cell, (2) starting physical disruption treatment while stirring said aqueous suspension, and then (3) adding an alkali while continuing stirring and physical disruption.

When an alkali is added to the suspension of a PHA-containing microbial cell without carrying out the physical disruption, nucleic acids, cell walls, cell membranes, insoluble proteins, etc. are flowed out from the microbial cell together with a PHA. At this time, the present inventors found that viscosity of the suspension significantly rose, and even stirring of the suspension became impossible in some conditions, thereby recovery of the PHA became impossible. Additionally, the present inventors found that a PHA was easily decomposed in recovering the PHA when a physical disruption (for example, cell disruption and emulsification by a high-pressure homogenizer) after an alkali addition to make pH level of the suspension to be 10 or higher. On the contrary, they unexpectedly found that a PHA was hardly decomposed when the physical disruption was carried out before the alkali addition.

Accordingly, in the present invention, it becomes possible to easily separate and recover a PHA from a suspension with inhibiting decomposition of the PHA by, in the step (a), once starting a physical disruption, and then gradually adding an alkali while continuing the physical disruption to promote solubilization or emulsification of the insoluble substances (cell substances) other than the PHA.

The aqueous suspension containing a PHA-containing microbial cell used in the step (a) means a suspension prepared by suspending the PHA-containing microbial cell obtained as above in water.

A suspension concentration of said microbial cell is preferably 500 g/L or less in terms of dried cell weight per liter of the aqueous suspension, and in view of stirring easiness of the suspension of microbial cell, more preferably 300 g/L or less. The lower limit is preferably 80 g/L or more.

The stirring means of the above aqueous suspension is not particularly restricted, but an emulsification-dispersion machine or a sonication disruption machine is preferably used for stirring to efficiently diffuse an alkali to be added and efficiently disrupting high-viscosity DNAs flowed out from the cell. More preferred is the emulsification-dispersion machine, and for example, SILVERSONMIXER manufactured by Silverson Machines, Inc., England, CLEAR MIX manufactured by M-TECHNIQUE, Japan, and Ebara Milder manufactured by Ebara Corporation, Japan, etc. may be used, but is not limited to these.

In the present invention, equipment for carrying out the physical disruption treatment is not particularly restricted, but there may be mentioned a high-pressure homogenizer, a sonication disruption machine, an emulsification-dispersion machine, a bead mill, etc. Among them, preferred is a high-pressure homogenizer, and more preferred are ones belonging to a type in which an aqueous suspension of the polymer is introduced into a pressure-resistant container having a micro-opening, and the suspension is pushed out from the opening by applying high pressure. As such equipment comprising a pressure-resistant container and a pressurization mechanism, for example, a high-pressure homogenizer manufactured by Italy Niro Soavi S.p.A is preferably used. Moreover, such equipment includes Bran+Luebbe continuous cell disruptioner (product of Bran+Luebbe GmbH, Germany), and Microfluidizer (product of Microfluidics, U.S.), etc., but it is not limited to these.

In such high-pressure homogenizers, since large shearing force is applied to a microbial cell, the microbial cell is efficiently destroyed and separation of a polymer is promoted. Moreover, in such equipment, since a high pressure is applied to the opening and becomes high temperature instantaneously, it is preferable to cool the microbial cell-containing suspension in a general cooling bath circulator, according to need, to prevent the temperature elevation and carry out a disruption treatment at 20 to 40° C. The molecular weight of a PHA hardly decreases when the treatment is carried out at such a comparatively low temperature. Therefore, in the preferable embodiment of the present invention, it is preferred to utilize a process comprising adding an alkali while carrying out a physical disruption at 20 to 40° C.

The alkali to be used in the step (a) is not particularly restricted provided that it is capable of disrupting a cell wall of the PHA-containing microorganism and discharging a PHA from inside to outside of the cell. The alkali includes, but not limited to, for example, alkali metal hydroxides such as sodium hydroxide, potassium hydroxide and lithium hydroxide; alkali metal carbonates such as sodium carbonate and potassium carbonate; alkali metal hydrogen carbonates such as sodium hydrogen carbonate and potassium hydrogencarbonate; alkali metal salts of organic acids such as sodium acetate and potassium acetate; alkali metal borates such as borax; alkali metal phosphates such as trisodium phosphate, disodium hydrogenphosphate, tripotassium phosphate and dipotassium hydrogenphosphate; alkaline earth metal hydroxides such as barium hydroxide; aqueous ammonia, etc. These may be used alone or two or more of them may be used in combination. Among these, alkali metal hydroxides and alkali metal carbonates are preferred since they are suitable for an industrial production and the costs are reasonable. And more preferred are sodium hydroxide, potassium hydroxide, lithium hydroxide, sodium carbonate and the like.

In the step (a) of the present invention, it is preferable to control the pH level during the addition of an alkali. The preferable pH range for efficiently solubilizing insolubilities (cell substances) derived from cells other than a PHA and having no adverse effect to the PHA itself is pH 9 to 13.5, and more preferably pH 10 to 13. If the pH level is higher than 13.5, molecular weight of a PHA tends to decrease, and if the pH level is below 9, the disruption effect tends to be reduced.

Therefore, a method may be preferably used, which comprises adding an alkali continuously or intermittently to a suspension of microbial cells while controlling the pH within the desired levels. In the present invention, controlling the pH in such manner prevents pH level from too much elevating, which will occur in the case of adding the whole alkali at once. Furthermore, constantly maintaining the alkali condition to be more than some extent makes it possible to maintain insoluble proteins to be a solubilizable state, and it becomes unnecessary to heat the suspension at a high temperature. As a result, the molecular weight decrease of a PHA may be prevented more efficiently.

The temperature on carrying out the step (a) is preferably from 10 to 45° C., and more preferably from 20 to 40° C. in view of preventing the molecular weight decrease of a PHA more efficiently.

As mentioned above, when a physical disruption such as high-pressure disruption is carried out while maintaining the pH to be an arbitrary level within 9 to 13.5 in the step (a), a treatment at such a low temperature as 20 to 40° C. becomes possible, and the molecular weight decrease might be suppressed to 10% or less even in the case of PHBH. Namely, it is particularly preferred to carry out the physical disruption in a pH level of 9 to 13.5, at 20 to 40° C. When the microbial cells are disrupted under such preferable alkali condition, more reproducible result may be obtained.

The separation of a PHA from the suspension may be carried out by, for example, centrifugation, membrane separation, filter filtration, etc.

In the followings, the step (a) is explained in further detail by using FIG. 1, which represents a schematic diagram showing preferable equipment for carrying out the step (a). Of course, the present invention is not limited to these equipment examples.

The reference numeral 1 in FIG. 1 indicates a microbial cell disruption equipment according to the invention as a whole. The reference numeral 6 indicates a pH control agent storage tank for reserving an alkali agent, and the agent in this pH control agent storage tank 6 is fed by a pump 4 to the cell disruption tank 11 through a pipeline 5 to adjust the pH of a microbial cell suspension in the cell disruption tank 11 according to need. This cell disruption tank 11 is equipped with a stirring means 2 for uniformly stirring and mixing the pH control agent, which is fed from the pH control agent storage tank 6, with the microbial cell suspension in the cell disruption tank 11. The cell disruption tank 11 is further equipped with a pH detection-control means composed of a pH meter 7 and a pH sensor-controller 3 for detecting the pH of the microbial cell suspension in the cell disruption tank 11 and controlling the rate of feed of the pH control agent by said pump 4 so that a predetermined pH level may be established. The cell disruption tank 11 works also as a cooling bath circulator, and the microbial cell suspension may be maintained at the desired constant temperature.

Referring to FIG. 1, the microbial cell suspension in the cell disruption tank 11 is fed via a pump 10 to a disruption equipment 9, where nucleic acids, which may be causative of viscosity elevation, is efficiently disrupted, and resultant mixture is fed to the cell disruption tank 11 via a pipeline 8. The added alkali is immediately diffused by the stirring means 2, and the microbial cell suspension is homogenized, thus making it possible to strictly control the pH level of the cell suspension. At this point, it is preferred to stir sufficiently in order to prevent the alkali concentration from becoming partially high, and a polymer would not be subjected to hydrolysis. The fluctuation range of the pH level to be controlled is preferably within ±1 of the set value, and more preferably within ±0.5. And it is preferred to control the pH including said fluctuation range to be within the above preferable pH range of 9 to 13.5.

Equipment which may be used as the disruption equipment 9, there may be mentioned high-pressure homogenizer, sonication disruption machine, emulsification-dispersion machine, beadmill, which are mentioned above, and the like. In addition, two or more of the same or different disruption machines may be installed in parallel or in series. It is preferable to use the above emulsification-dispersion machine or sonication disruption machine as the stirring means 2 for efficiently diffusing the added alkali and for efficiently disrupting high-viscosity DNAs flowed out from the cell. In-line mixer type of these machines is also manufactured, and those may function as both the pump 10 and stirring means 2 in FIG. 1, for example. In that case, the structure advantageously becomes simple. In addition, general-purpose equipment may be used as the pH meter 7 and the pH detection and control equipment 3.

Next, the step (b) in the present invention is a purifying method of a PHA which comprises treating with either an enzyme or a surfactant, or using both in combination.

In the present invention, effects may be more remarkable as described below by carrying out treatment of the step (b) to the PHA having relatively high purity obtained in the step (a).

It is generally considered that proteins, peptidoglycan (a cell wall component), lipids, polysaccharides, nucleic acids and other hydrocarbons are adhered to the PHA particles obtained in the step (a). The step (b) of the present invention is carried out for improving the purity of a PHA by removing at least several of the above adherent components.

The preferred practice of the present invention, a PHA separated in the step (a) is used in the following step (b), not in a dried state obtained by the separated PHA, but in such a state as suspended in water, or as wetted with water after carrying out, e.g., centrifugation or membrane separation, for improving the treatment effect of the step (b).

When the treatment is carried out with an enzyme in the step (b), the enzyme to be used includes proteases, lipid degrading enzymes, cell wall degrading enzymes and DNases. As specific examples thereof, the following enzymes may be listed. These may be used alone or two or more of them may be used in combination.

(1) Proteases
Alcalase, pepsine, trypsin, papain, chymotrypsin, aminopeptidase, carboxypeptidase, etc.

(2) Lipid Degrading Enzymes
Lipases, phospholipases, cholinesterases, phosphatases, etc.

(3) Cell Wall Degrading Enzymes
Lysozyme, amylase, cellulase, maltase, saccharase, α-glycosydase, β-glycosydase, N-glycosydase, etc.

(4) DNases
Ribonuclease, etc.

The enzymes to be used in this step are not restricted to the above ones, but may include any enzymes provided that they are usable for industrial products. Moreover, commercially available cleaning enzyme detergents, etc. may also be used.

Furthermore, it may be an enzyme composition containing e.g. a stabilizing agent of enzymes or an anti-redeposition agent, together with an enzyme, and is not restricted to a simple enzyme.

As the enzyme used for the purpose of decomposing and removing insoluble protein and insoluble peptidoglycan adhering to the PHA, at least one species selected from proteases and cell wall decomposition enzymes are preferred, and proteases are more preferred.

As a preferable protease, there may be mentioned, among those included in the above exemplifications, Protease A, Protease P, Protease N (products of Amano Enzyme Inc.), Alkalase, Savinase, Everlase (products of Novozymes Inc.), etc. as industrially applicable ones, and these are suitable also in view of decomposition activity. Moreover, lysozyme or the like is preferably used as the cell wall decomposition enzyme among those included in the above exemplification. But the enzymes are not limited to these.

When carrying out an enzyme treatment, the treatment should be naturally carried out at a temperature lower than the denaturation temperature of the enzyme. In many cases, the denaturation temperature of an enzyme is lower than 65° C. Some enzymes have the denaturation temperature higher than 65° C., and when using such enzymes, it is possible to carry out the treatment at a temperature higher than 65° C. However, taking the molecular weight decrease of a PHA into consideration, the temperature of the enzyme treatment is preferably 50° C. or less, and more preferably 20° C. to 50° C.

The enzyme treatment is preferably continued until the treatment proceeds to the required level, and it generally requires 0.5 to 2 hours.

The amount of the enzyme to be used depends on the species and activity thereof. Although there is no particular restriction, but it is preferably 0.001 to 10 parts by weight per 100 parts by weight of the polymer, and more preferably 0.001 to 5 parts by weight or less in view of cost.

The method of the present invention is advantageous as compared with a conventional method comprising treating the PHA-containing cell itself with an enzyme and disrupting the cell (see Japanese Kokoku Publication Hei-04-61638), in that a PHA may be produced in a low cost since only an amount of the enzyme to solubilize insolubilities slightly remaining in the PHA is required.

In the step (b) of the present invention, it is possible to use a surfactant as a solubilizing agent for removing impurities adhering to the PHA particles.

As the surfactant to be used in the present invention, there may be mentioned an anionic surfactant, a cationic surfactant, an ampholytic surfactant, a nonionic surfactant, or the like. These may be used alone or two or more of them may be used in combination.

As the anionic surfactant, there may be mentioned an alkyl sulfate, an alkyl benzene sulfonate, an alkyl or alkenyl sulfate, an alkyl or alkenyl ether sulfate, an α-olefin sulfonate, an α-sulfofatty acid salt or an ester thereof, an alkyl or alkenyl ether carboxylate, an amino acid surfactant, an N-acyl amino acid surfactant, etc. Preferred among these are an alkyl sulfate having 12 to 14 carbon atoms in an alkyl group, a straight chain alkyl benzene sulfonate having 12 to 16 carbon atoms in the alkyl group, and an alkyl sulfate or alkyl ether sulfate having 10 to 18 carbon atoms in the alkyl group. The counter ion preferably includes, but not limited to, alkali metals such as sodium and potassium, alkaline earth metals such as magnesium, alkanolamines such as monoethanolamine, diethanolamine and triethanolamine.

As the cationic surfactant, there may be mentioned an alkyltrimethyl ammonium salt, a dialkyldimethyl ammonium salt, etc.

As the ampholytic surfactant, there may be mentioned a carbobetaine surfactant, a sulfobetaione surfactant, etc.

As the nonionic surfactant, there may be mentioned a polyoxyalkylene (preferably oxyethylene) alkyl or alkenyl ether, a polyoxyalkylene (preferably oxyethylene) alkyl- or alkenylphenyl ether, a polyoxyethylene polyoxypropylene alkyl or alkenyl ether, polyoxyethylene polyoxypropylene glycol, polyethyleneglycol, a polyoxyethylenealkylamine, a higher fatty acid alkanolamide, an alkylglucoside, an alkylglucosamide, an alkylamine oxide, etc. Among these, preferred are those having high hydrophilicity and those with a low formation ability of liquid crystals, which is formed when admixed with water, or those which generate no liquid crystals. Also use of a polyoxyalkyl ether having 10 to 14 carbon atoms and a polyoxyethylene alkyl ether having 10 to 14 carbon atoms, polyethylene glycol, etc. are preferably used since they have comparatively preferable biodegradability, but is not limited to these.

Specifically among the above-mentioned surfactants, preferred are anionic surfactants such as sodium dodecyl sulfate, sodium dodecylbenzene sulfonate, sodium cholate, sodium deoxycholate and sodium oleate; and nonionic surfactants such as polyethylene glycol and a polyoxyethylene alkyl ether having 10 to 14 carbon atoms, etc. in view of cost, amount to be used and effects produced by addition thereof. Two or more of these may also be preferably used in combination.

The surfactants mentioned here in above are used in a general commercially available detergent, and an appropriate detergent for cleaning may be used as the surfactant.

In view of detergency, preferred are an anionic surfactant and a nonionic surfactant. For the purpose of washing and removing protein etc., it is preferable to use an anionic surfactant, and for the purpose of washing and removing fatty acid and oil, or when an enzyme is used in combination, a nonionic surfactant is preferably used. Furthermore, both an anionic surfactant and a nonionic surfactant may be contained. When both of them are contained, the weight ratio of the anionic surfactant/the nonionic surfactant is preferably 1/100 to 100/10, more preferably 5/100 to 100/20, still more preferably 5/100 to 100/100, and particularly preferably 5/100 to 50/100.

The addition amount of the surfactant is not particularly restricted, but it is preferably 0.001 to 10 parts by weight per 100 parts by weight of a polymer, and more preferably it is 0.001 to 5 parts by weights in view of cost.

In addition, the treatment temperature in the surfactant treatment is not particularly restricted, but preferably in the range of 20 to 50° C. in view of promoting solubirization of cell components other than a PHA. The treatment period is preferably 1 minute to 2 hours.

As a preferable embodiment of the present invention, there may be mentioned a method comprising use of a surfactant with an enzyme treatment in combination because a higher purification effect may be produced.

When an enzyme treatment and a surfactant are applied in combination, the amounts of the enzyme and the surfactant to be used are the same as the above, respectively. The treatment temperature is preferably 20 to 50° C., and the treatment period is preferably 1 minute to 2 hours.

The present inventors acknowledge the remarkable effects which are produced when the two agents are used combinedly. The reason why the effects are produced may be considered that a surfactant would efficiently remove a decomposed product which is released and becomes insoluble by the enzyme decomposition, or that the structure of a protein would be changed by a surfactant to be susceptible to an enzyme decomposition. In this case, the surfactant and the enzyme may be separately prepared and appropriately admixed to use, but the commercially available detergent containing an enzyme may be used as it is, since it is a mixture comprising a surfactant and an enzyme.

In the step (b) of the present invention, the enzyme or surfactant treatment to be carried out may be freely selected according to reasons or objects based on species of impurities to be removed, cost or other restrictions on the process, the purity of the objective PHA and/or the like.

The enzyme treatment may be carried out in some divided steps. For example, one enzyme is used in the first step and subsequently the same or different enzyme may be used in the following step. When one or more species of enzymes are used, it is convenient to treat a PHA in a single step using a mixture of enzymes if the contained enzymes do not digest each other. Moreover, as mentioned above, the surfactant and enzyme treatment maybe carried out at the same time. Furthermore, it is preferred to carry out both the enzyme treatment and the surfactant treatment with stirring.

In the present invention, PHA particles obtained by the above-mentioned treatment in the step (b) is washed with a hydrophilic solvent and/or water for degreasing, deodorization and decolorization.

The hydrophilic solvent to be used in the step (b) is not particularly restricted, but specifically, there may be mentioned methanol, ethanol, acetone, acetonitrile, tetrahydrofuran, etc. Among these hydrophilic solvents, methanol and ethanol are particularly preferred since they are cheap and have a good detergency.

In addition, the above hydrophilic solvents may be used as a mixture with water. When using a mixed solvent composed of water and a hydrophilic solvent, the mixing volume ratio between water and the hydrophilic solvent (water/hydrophilic solvent) is preferably about 4/6 to 0.5/9.5.

The amount of the above hydrophilic solvent used for washing is not particularly restricted, but preferably not less than the amount equal to the polymer volume.

The temperature in washing is preferably not less than 20° C. but less than 60° C.

By washing a PHA with the above hydrophilic solvent and/or water, a PHA having more improved purity may be isolated.

In the present invention, it is possible to recover a PHA when the step (b) is completed, and the recovered PHA can be used as a material for molding and the like.

Since the PHA obtained in the step (b) is a fine microparticle having the particle diameter of as small as several microns, it is desirable to agglomerate the PHA to have a suitable particle diameter in the step (c), as described below, in view of separatability, handling property, etc.

The step (c) of the present invention comprises agglomerating PHA particles by simple and convenient operations such as suspending the PHA purified in the step (b) in a hydrophilic solvent and/or water, and stirring said suspension at a temperature equal to or below the boiling point to enlarge the particle diameter.

The hydrophilic solvent to be used in the step (c) is not particularly restricted, but there may be mentioned, for example, alcohols such as methanol, ethanol, 1-propanol, 2-propanol and butanol; ketones such as acetone and methylethylketone; ethers such as tetrahydrofuran and dioxane; nitriles such as a cetonitrile and propiononitrile; amides such as dimethylformamide and acetoamide; dimethylsulfoxide, pyridine, piperidine and the like.

Preferred among them are methanol, ethanol, 1-propanol, 2-propanol, butanol, acetone, methylethylketone, tetrahydrofuran, dioxane, acetonitrile, propiononitrile, etc. in view of their removability. More preferred are methanol, ethanol, 1-propanol, 2-propanol, butanol, acetone, tetrahydrofuran, acetonitrile, etc. in view of their ready availability.

Still more preferred is to use the solvent used for washing the PHA in the step (b), since it becomes possible to reduce equipment cost and the like because it becomes possible to proceed to the agglomeration process continuously, and/or because only one solvent tank is required. Therefore, as preferred solvents, there may be mentioned methanol, ethanol, acetone, acetonitrile, tetrahydrofuran, and the like. Among these, particularly preferred are methanol and ethanol since they are cheap and have good detergency.

Furthermore, the above hydrophilic solvent may be mixed with water to be used.

That is, the medium of a suspension may be any of a simple hydrophilic solvent, simple water, or a mixed solvent comprising a hydrophilic solvent and water. And preferred is the mixed solvent comprising the hydrophilic solvent and water. The concentration of the hydrophilic solvent in the mixed solution is preferably 10 weight % or more and more preferably 20 weight % or more in order to obtain more sufficient agglomerating effect. On the other hand, the upper limit of the concentration of the hydrophilic solvent is 99 weight % or less, preferably 98 weight % or less, and more preferably 97 weight % or less.

The concentration of a PHA in the suspension of the step (c) is not particularly restricted, but preferably 1 g/L or more, more preferably 10 g/L or more, and still more preferably 30 g/L or more. The upper limit is preferably 500 g/L or less, more preferably 300 g/L or less, and still more preferably 200 g/L or less in view of securing fluidity of the PHA suspension.

Stirring means in the step (c) of the present invention is not particularly restricted and includes a stirring bath, etc. which causes turbulent flow.

The temperature on agglomeration in the step (c) of the present invention is preferably a room temperature (about 24° C.) or higher, more preferably 40° C. or higher, and still more preferably 60° C. or higher. The upper limit is not particularly limited, and any temperatures up to the boiling point of said suspension may be selected.

The step (c) maybe carried out under a condition of either normal pressure or high pressure. In the step (c) of the present invention, it is usually possible to cause agglomeration in such a very short time as about several minutes, therefore there is no need to worry about the molecular weight decrease depending on a temperature when PHA is isolated soon after the agglomeration by filtration or the like.

By the agglomerating method of the step (c) according to the present invention, it becomes possible to enlarge the particle diameter of a PHA. For example, an agglomerate having the weight average diameter of 10 μm or more, preferably 50 μm or more, and more preferably 100 μm or more may be obtained. The upper limit is not particularly limited, but it is an agglomerate having the weight average diameter of 5000 μm or less, and preferably 3000 μm or less.

With increase of the particle diameter, recovery by filtration becomes easy, and thus the equipment cost may be reduced in an industrial production. Herein, the method for filtration is not particularly restricted, but for example, a filter, a basket type separator, etc. may be used.

To the PHA obtained by the present invention, coloring agents such as pigments and dyes, fillers such as inorganic or organic particles, glass fibers, whiskers and mica, stabilizing agents such as antioxidants and ultraviolet absorbents, lubricants, mold-release agents, water-repellents, antibacterials, and other subsidiary additive agents may be added to prepare a PHA resin composition.

The said PHA resin composition may be formed into various forms, such as fibers, threads, ropes, textiles, fabrics, nonwoven fabrics, papers, films, sheets, tubes, boards, sticks, containers, bags, parts, foamed bodies, etc. Moreover, it may be also processed into a biaxial stretched film. The formed products may be suitably used for such fields as agriculture, fishery, forestry, gardening, medical, sanitary products, clothing, non-clothing, packaging, and others. In particular, since the PHA obtained by the method of the present invention has quite high purity, it is excellent in that it may be applied to fields requiring high purity, which a PHA obtained by the conventional methods cannot be applied, for example, fields of film, medical, sanitary products, etc.

As mentioned above, by the recovery method of the present invention, it becomes possible to efficiently recover a high-purity PHA from a PHA-containing microbial cell, which has been very difficult until now, and a PHA may be produced and provided at a low cost in a industrial scale.

By using the method for recovering a PHA comprising steps (a) and (b) according to the present invention, a polyhydroxyalkanoate is efficiently recovered in high purity from a polyhydroxyalkanoate-producing microbial cell, and is produced and provided in a low cost on an industrial scale. And by further carrying out the step (c), it is possible to obtain an agglomerate of the PHA particles.

BEST MODE FOR CARRYING OUT THE INVENTION

The following Examples illustrates the present invention in further detail, but the invention is by no means limited to these.

The measuring method for each property is described below.

(Method to Measure 3HH mol %)

A PHA (PHBH) in a microbial cell after completion of culture was recovered by chloroform extraction and hexane crystallization, and was subjected to analysis. The measurement of 3HH mol % was carried out by the method described in Example 1 of Japanese Kokai Publication 2001-340078. That is, PHBH was suspended in 2 ml of sulfuric acid-methanol mixed solution (15:85), chloroform (2 ml) was added thereto, and the suspension was heated to 100° C. for 140 minutes. After cooling the suspension, 1 ml of distilled water was added and a chloroform layer was recovered after stirring. This chloroform layer was subjected to composition analysis using Shimadzu's gas chromatograph GC-17A (NEUTRA BOND column produced by GL Science Inc.).

(Measuring Method for Residual Amount of Nitrogen in the PHA)

Just before the measurement, the recovered PHA (PHBH) was dried under reduced pressure at 50° C. for 5 hours, and the total nitrogen amount was measured using trace nitrogen analyzer TN-10 (product of Dia Instruments Co., Ltd.). In the present invention, the measured nitrogen concentration was converted to a corresponding protein concentration by multiplying 6.38.

(Measuring Method for the Average Molecular Weight of the PHA)

After dissolving 10 mg of the recovered dried PHA in 5 ml of chloroform, insoluble matters were removed by filtration. Resultant solution was analyzed using Shimadzu's GPC system equipped with Shodex K805L (300×8 mm, 2 columns-connected) (product of Showa Denko K. K.) with chloroform as a mobile phase. As the molecular weight standard sample, commercially available standard polystyrene was used. The molecular weight of a PHA in the microbial cell after completion of culture was measured in the same manner as in the above method to measure 3HH mol %, that is, by recovering a PHA from a PHA-containing microbial cell by chloroform extraction and hexane crystallization.

(Measurement of the Particle Diameter)

The average particle diameter of a PHA particle was measured by using a microtrac particle diameter analyzer (product of NIKKISO Co., Ltd., FRA). An aqueous suspension of the PHA was adjusted to the predetermined concentration, and the particle diameter corresponding to 50% accumulation amount of whole particles was determined as the average particle diameter.

EXAMPLE 1

(1) Step (a) Treatment

PHBH was produced by culturing *Ralstonia eutropha* obtained by introducing a PHA synthase group gene derived from *Aeromonas caviae* (accession number FERM BP-6038) according to the method described in Example 1 of Japanese Kokai Publication 2001-340078. After completion of the culture, microbial cells were recovered by centrifugation to obtain an aqueous suspension containing 100 g/L of dried cells. The average molecular weight of PHBH in the recovered microbial cells was 1,400,000 and 3HH composition was 6.8 mol %.

This aqueous suspension was subjected to a cell physical disruption under an alkali condition using the cell disruption equipment of FIG. 1. The cell disruption tank 11 was charged with 600 ml of aqueous suspension of the PHA-containing microbial cell, and then the reaction tank was connected to high-pressure homogenizer model PA2K (disruption equipment 9) manufactured by Italy Niro Soavi S.p.A, followed by carrying out homogenization at a pressure of 600 to 700 kgf/cm$^2$. By gradually adding 10% of sodium hydroxide after the lapse of 10 minutes, the cell aqueous suspension was adjusted to pH 12.5, and the suspension was circulated between the disruption tank 11 and the disruption equipment 9 while maintaining this pH level. During this period, the temperature of the cell disruption tank was maintained at 30° C. by a thermoregulated circulation pump. Control of the pH level was carried out as the followings; the pH electrode (pH indicator 7) was immersed in the suspension in the cell disruption tank 11 and connected to Labo Controller MDL-6C manufactured by B. E. Marubishi Co., Ltd., and operation parameters were set so that when the pH level of said suspension had dropped below a set value, a peristaltic pump (pump 4) would be actuated to deliver an aqueous solution of sodium hydroxide into the suspension until the set value is attained. After 10 time-circulations between the disruption tank 11 and the disruption equipment 9, the suspension was centrifuged (9500 g, 30 minutes) to obtain a PHBH fraction. The obtained PHBH fraction was washed with water twice, and was finally made into an aqueous suspension containing 100 g/L of dried PHBH, and the aqueous suspension was used in the next step.

(2) Step (b) Treatment

The following tested agents were added to each 60 ml of PHBH suspension obtained in the above (1). The addition amounts of the following tested agents are all indicated as weight % relative to the polymer weight in a suspension.
(1) 5 weight % of sodium dodecyl sulfate (SDS) (product of Wako Pure Chemical Industries, Ltd.)
(2) 0.08 weight % of Protease N (Product of Amano Enzyme Inc.)
(3) 5 weight % of SDS and 0.08 weight % of Protease N
(4) 5 weight % of SDS and 0.08 weight % of egg white lysozyme (product of Wako Pure Chemical Industries, Ltd.)
(5) 5 weight % of SDS, 0.08 weight % of Protease N and 0.08 weight % of egg white lysozyme
(6) 5 weight % of a synthetic detergent for cleaning (trade name: Attack, product of Kao Corp.) (the amount is calculated to be such an amount to contain an enzyme component of about 0.5 weight %)

Each of said suspension was stirred for 1 hour at 50° C. and pH of 7.0. Thereafter, PHBH was recovered by centrifugation, washed with 60 ml of water twice and with 60 ml of ethanol twice, and dried at 50° C. under reduced pressure to obtain a PHBH powder.

In addition, as a sample without the treatment of the step (b), a PHBH powder obtained by washing the PHBH obtained in the above (1) with ethanol twice and drying under reduced pressure was used. The results are shown in Table 1.

TABLE 1

| Sample | Total amount of nitrogen μg/g | Total amount of protein mg/g | PHA purity (%) |
|---|---|---|---|
| Without treatment | 5500 | 35.09 | 96.49 |
| ① SDS | 600 | 3.83 | 99.62 |
| ② Protease N | 540 | 3.45 | 99.66 |
| ③ SDS + Protease N | 130 | 0.83 | 99.92 |
| ④ SDS + Lysozyme | 69 | 0.44 | 99.96 |
| ⑤ SDS + Protease N + Lysozyme | 110 | 0.70 | 99.93 |
| ⑥ Synthetic powdered detergent | 190 | 1.21 | 99.88 |

PHBH showed purity of 99.5% or more in the step (b), and was conformed to have an effect as compared with that conducted no treatment. Although use of SDS alone was effective, the purity was further improved by using an enzyme in combination. Moreover, the commercially available synthetic detergent is considered to be preferable since it also has a good effect and is cheap.

EXAMPLE 2

Carrying out the Recovery Process in a Total Flow
(Steps (a) Through (c))

*Ralstonia eutropha* cultured in the same manner as in Example 1(1) was recovered by centrifugation. This cell was suspended in water to prepare an aqueous suspension containing 100 g/L of dried cells. The average molecular weight of PHBH in the recovered cells was about 1,470,000 and 3 HH composition was 5.1 mol %. Using 400 ml of this suspension, a high-pressure disruption according to the method described in Example 1(1) was carried out while maintaining pH at about 12.5. After completion of the treatment, a PHBH fraction was recovered by centrifugation, and washed with water twice.

The obtained PHBH fraction was suspended in water to prepare an aqueous suspension containing 100 g/L of dried cells. To this suspension, 0.2 weight % of Protease N, 0.2 weight % of lysozyme and 4 weight % of SDS relative to the polymer weight were added, and stirred at 50° C. and pH of 7.0 for 1 hour. After completion of the treatment, PHBH was washed with water twice.

The obtained PHBH fraction was suspended in water to prepare an aqueous suspension with a concentration of 200 g/L. 290 ml of 95% ethanol was added and suspended in said suspension, and successively PHBH was precipitated by centrifugation. 290 ml of the supernatant was removed, and 290 ml of 95% ethanol was added again to the polymer fraction to suspend PHBH. This ethanol washing was carried out twice, and a suspension added with 290 ml of 95% ethanol was prepared. Said PHBH suspension was gradually added to 290 ml of ethanol at 70° C. in 15 minutes, and PHBH was agglomerated by further stirring for 10 minutes after completion of addition. The agglomerated PHBH was recovered by filtration using Kiriyama filter paper (No. 58) (product of Kiriyama Glass Works Co.). PHBH on the filter paper was washed with 120 ml (equal amount to PHBH content) of 95% ethanol twice. The obtained PHBH was dried in vacuum at 50° C. The results of the PHBH purity analysis are shown in Table 2.

TABLE 2

| PHBH | Total amount of nitrogen μg/g | Total amount of protein mg/g | Purity (%) | Particle size μm | Molecular weight ×10$^{-6}$ |
|---|---|---|---|---|---|
| After step (b) | — | — | — | 7.5 | 1.47 |
| After step (c) | 140 | 0.89 | 99.91 | 203 | 1.42 |

As the result, 56 g of PHBH having the purity of 99.91% was obtained (recovery percentage from the material before the step (a) is 93%). The average molecular weight after the step (c) was 1,420,000, which meant that decrease was only 3.4% from the molecular weight from the material before the step (a).

POSSIBILITY OF INDUSTRIAL APPLICATION

Using the method for recovering a PHA comprising the steps (a) and (b) of the present invention, it becomes possible to efficiently recover a high-purity PHA from a PHA-containing microbial cell, and PHA may be produced and provided at a low cost in an industrial scale. Moreover, by using the step (c) agglomerated PHA particles may be obtained.

The invention claimed is:

1. A method for recovering a polyhydroxyalkanoate from a polyhydroxyalkanoate-containing microbial cell
   which comprises the following steps (a) and (b);
   (a) a step comprising adding an alkali to an aqueous suspension of the polyhydroxyalkanoate-containing microbial cell while stirring and carrying out a physical disruption treatment to disrupt the cell, solubilizing or emulsifying cell substances other than the polyhydroxyalkanoate in said cell, and then separating the polyhydroxyalkanoate from the aqueous suspension, and
   (b) a step comprising treating the separated polyhydroxyalkanoate with an enzyme and/or a surfactant to solubilize impurities adhering to the polyhydroxyalkanoate or to solubilize them after decomposing, and then washing the polyhydroxyalkanoate with a hydrophilic solvent and/or water.

2. The method for recovering a polyhydroxyalkanoate according to claim 1
   which further comprises the following step (c);
   (c) a step comprising suspending the washed polyhydroxyalkanoate in a hydrophilic solvent and/or water and stirring at a temperature equal to or below the boiling point of said suspension and agglomerating the polyhydroxyalkanoate to enlarge the particle diameter thereof, and then separating the agglomerated polyhydroxyalkanoate from the suspension.

3. The method for recovering a polyhydroxyalkanoate according to claim 1,
   wherein the polyhydroxyalkanoate is a copolymer obtainable by copolymerizing at least two species of hydroxyalkanoate monomers selected from the group consisting of 3-hydroxybutyrate, 3-hydroxyvalerate, 3-hydroxypropionate, 4-hydroxybutyrate, 4-hydroxyvalerate, 5-hydroxyvalerate, 3-hydroxypentanoate, 3-hydroxyhexanoate, 3-hydroxyheptanoate, 3-hydroxyoctanoate, 3-hydroxynonanoate and 3-hydroxydecanoate.

4. The method for recovering a polyhydroxyalkanoate according to claim 3,
wherein the polyhydroxyalkanoate is a copolymer composed of 3-hydroxyhexanoate and at least one species among said hydroxyalkanoate monomers other than 3-hydroxyhexanoate.

5. The method for recovering a polyhydroxyalkanoate according to claim 4,
wherein the polyhydroxyalkanoate is a copolymer composed of 3-hydroxyhexanoate and 3-hydroxybutyrate.

6. The method for recovering a polyhydroxyalkanoate according to claim 1,
wherein, in the step (a), the physical disruption treatment is carried out by a high-pressure homogenizer.

7. The method for recovering a polyhydroxyalkanoate according to claim 1,
wherein, in the step (a), the alkali is added continuously or intermittently while controlling a pH level.

8. The method for recovering a polyhydroxyalkanoate according to claim 7,
wherein, in the step (a), the pH level is controlled between 9 and 13.5.

9. The method for recovering a polyhydroxyalkanoate according to claim 1,
wherein the alkali to be used in the step (a) is at least one species selected from the group consisting of sodium hydroxide, potassium hydroxide, lithium hydroxide and sodium carbonate.

10. The method for recovering a polyhydroxyalkanoate according to claim 1,
wherein the enzyme to be used in the step (b) is at least one species selected from the group consisting of proteases, lipid degrading enzymes, cell wall degrading enzymes and DNases.

11. The method for recovering a polyhydroxyalkanoate according to claim 1,
wherein the surfactant to be used in the step (b) is at least one species selected from the group consisting of anionic surfactants, cationic surfactants, ampholytic surfactants and nonionic surfactants.

12. The method for recovering a polyhydroxyalkanoate according to claim 1,
wherein the hydrophilic solvent to be used for the washing in the step (b) is at least one species selected from the group consisting of methanol, ethanol, acetone, acetonitrile and tetrahydrofuran.

13. The method for recovering a polyhydroxyalkanoate according to claim 2,
wherein the hydrophilic solvent used in the step (c) is at least one species selected from the group consisting of methanol, ethanol, acetone, acetonitrile and tetrahydrofuran.

14. The method for recovering a polyhydroxyalkanoate according to claim 1,
wherein a microorganism containing the polyhydroxyalkanoate is a microorganism selected from the group consisting of species belonging to the genus *Aeromonas, Alcaligenes, Azotobacter, Bacillus, Clostridium, Halobacterium, Nocardia, Rhodospirillum, Psuedomonas, Ralstonia, Zoogloea, Escherichia, Candida, Saccharomyces* and *Yarrowia*.

15. The method for recovering a polyhydroxyalkanoate according to claim 14,
wherein the microorganism containing the polyhydroxyalkanoate is *Aeromonas caviae*.

16. The method for recovering a polyhydroxyalkanoate according to claim 1, wherein the microorganism containing the polyhydroxyalkanoate is a transformant obtainable by introducing a polyhydroxyalkanoate synthase group gene derived from *Aeromonas caviae*.

17. The method for recovering a polyhydroxyalkanoate according to claim 16,
wherein the microorganism containing the polyhydroxyalkanoate is *Ralstonia eutropha* obtainable by introducing a polyhydroxyalkanoate synthase group gene derived from *Aeromonas caviae*.

18. The method for recovering a polyhydroxyalkanoate according to claim 2,
wherein the polyhydroxyalkanoate is a copolymer obtainable by copolymerizing at least two species of hydroxyalkanoate monomers selected from the group consisting of 3-hydroxybutyrate, 3-hydroxyvalerate, 3-hydroxypropionate, 4-hydroxybutyrate, 4-hydroxyvalerate, 5-hydroxyvalerate, 3-hydroxypentanoate, 3-hydroxyhexanoate, 3-hydroxyheptanoate, 3-hydroxyoctanoate, 3-hydroxynonanoate and 3-hydroxydecanoate.

19. The method for recovering a polyhydroxyalkanoate according to claim 18,
wherein the polyhydroxyalkanoate is a copolymer composed of 3-hydroxyhexanoate and at least one species among said hydroxyalkanoate monomers other than 3-hydroxyhexanoate.

20. The method for recovering a polyhydroxyalkanoate according to claim 2,
wherein, in the step (a), the physical disruption treatment is carried out by a high-pressure homogenizer.

* * * * *